United States Patent
Sakagawa et al.

(10) Patent No.: US 9,852,269 B2
(45) Date of Patent: Dec. 26, 2017

(54) DIAGNOSIS SUPPORT APPARATUS, METHOD OF CONTROLLING DIAGNOSIS SUPPORT APPARATUS, AND PROGRAM THEREFOR

(75) Inventors: Yukio Sakagawa, Tokyo (JP); Hiroshi Imamura, Tokyo (JP); Akihiro Katayama, Yokohama (JP); Hiroyuki Shinbata, Tama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 847 days.

(21) Appl. No.: 12/738,577

(22) PCT Filed: Sep. 9, 2008

(86) PCT No.: PCT/JP2008/066238
§ 371 (c)(1),
(2), (4) Date: Apr. 16, 2010

(87) PCT Pub. No.: WO2009/050962
PCT Pub. Date: Apr. 23, 2009

(65) Prior Publication Data
US 2010/0250275 A1    Sep. 30, 2010

(30) Foreign Application Priority Data

Oct. 18, 2007 (JP) .................................. 2007-271300

(51) Int. Cl.
*G06Q 50/22* (2012.01)
*A61B 6/00* (2006.01)
(Continued)

(52) U.S. Cl.
CPC .............. *G06F 19/345* (2013.01); *A61B 6/00* (2013.01); *G06F 19/321* (2013.01);
(Continued)

(58) Field of Classification Search
CPC ............ A61B 6/027; A61B 8/12; A61B 17/42; A61B 17/425; A61B 18/14; A61B 18/18;
(Continued)

(56) References Cited

U.S. PATENT DOCUMENTS 5,260,871 A * 11/1993 Goldberg ...................... 600/320
5,289,374 A    2/1994 Doi et al.
(Continued)

FOREIGN PATENT DOCUMENTS

JP    2001-357381 A    12/2001
JP    3417595 B    6/2003
(Continued)

OTHER PUBLICATIONS

Kawata et al., "Curvature Based Internal Structure Analysis of Pulmonary Nodules Using Thoracic 3-D CT Images", the transactions of the Institute of Electronics, Information and Communication Engineers D-II, vol. J83-D-II, No. 1, pp. 209-218, Jan. 2000.
(Continued)

*Primary Examiner* — Eliza Lam
(74) *Attorney, Agent, or Firm* — Carter, DeLuca, Farrell & Schmidt, LLP

(57) ABSTRACT

A diagnosis support system which performs computer processing of data obtained from an object to be examined and presents the obtained diagnostic information is disclosed. The diagnosis support apparatus includes a diagnosis support processing unit which processes data obtained from the object to extract diagnosis support information, a storage unit which stores the examination history of the object, and a changing unit which changes a processing method in the diagnosis support processing unit in accordance with the examination history of the object stored in the storage unit. In at least one embodiment, diagnosis processing is executed to obtain medical diagnostic information by performing
(Continued)

computer processing of data obtained from the object, and the processing method for diagnosis support processing is changed in accordance with the examination history of the object.

8 Claims, 7 Drawing Sheets

(51) Int. Cl.
*G06F 19/00* (2011.01)
*G06T 7/00* (2017.01)

(52) U.S. Cl.
CPC ......... *G06F 19/3443* (2013.01); *G06Q 50/22* (2013.01); *G06T 7/0012* (2013.01); *G06F 19/3431* (2013.01); *G06T 2207/30004* (2013.01)

(58) Field of Classification Search
CPC . A61B 18/1815; A61B 18/20; A61B 1/00016; A61B 1/00034; A61B 1/00096; A61B 1/00135; A61B 1/00142; A61B 1/00
USPC ........ 600/320, 407, 549; 382/128, 132, 133, 382/190, 217, 106, 103; 705/2–3; 702/19
See application file for complete search history.

(56) References Cited

U.S. PATENT DOCUMENTS

| | | | |
|---|---|---|---|
| 6,075,879 A * | 6/2000 | Roehrig et al. | 382/132 |
| 6,418,238 B1 * | 7/2002 | Shiratani et al. | 382/133 |
| 7,162,063 B1 * | 1/2007 | Craine et al. | 382/128 |
| 7,483,919 B2 * | 1/2009 | Galperin | |
| 7,640,051 B2 * | 12/2009 | Krishnan et al. | 600/407 |
| 7,876,938 B2 * | 1/2011 | Huang et al. | 382/128 |
| 7,876,939 B2 * | 1/2011 | Yankelevitz et al. | 382/128 |
| 8,045,805 B2 * | 10/2011 | Ramsay et al. | 382/190 |
| 2003/0120133 A1 | 6/2003 | Rao et al. | |
| 2004/0122702 A1 * | 6/2004 | Sabol et al. | 705/2 |
| 2005/0149360 A1 * | 7/2005 | Galperin | 705/2 |
| 2005/0201607 A1 | 9/2005 | Sato et al. | |
| 2006/0064248 A1 * | 3/2006 | Saidi et al. | 702/19 |
| 2007/0100226 A1 * | 5/2007 | Yankelevitz et al. | 600/407 |
| 2007/0112716 A1 * | 5/2007 | Sapir et al. | 706/47 |
| 2008/0033894 A1 * | 2/2008 | Steck et al. | 706/12 |
| 2008/0292194 A1 * | 11/2008 | Schmidt et al. | 382/217 |
| 2009/0043223 A1 * | 2/2009 | Zhang et al. | 600/549 |

FOREIGN PATENT DOCUMENTS

| | | |
|---|---|---|
| JP | 2003-325458 A | 11/2003 |
| JP | 2004-046594 A | 2/2004 |
| JP | 2005-284846 A | 10/2005 |
| JP | 2005270635 | 10/2005 |
| JP | 2005-334219 A | 12/2005 |
| JP | 2008-102665 A | 5/2008 |

OTHER PUBLICATIONS

"Determination criteria and follow-up guidelines for lung cancer CT screening by single slice helical CT", The Japanese Society of CT Screening (NPO), published Jan. 4, 2005, 25 pages including original Japanese language publication and an English translation summary thereof have been submitted.

European search report issued in corresponding application No. 08840701.0 dated Nov. 7, 2016.

* cited by examiner

FIG. 6

| IMAGING RANGE | ORGAN NAME | DISEASE NAME | IMPORTANT MORBIDITY | PROGRESS DEGREE (STAGE) | ASSOCIATED DISEASE NAME |
|---|---|---|---|---|---|
| CHEST | LUNG | MALIGNANT TUMOR | 10 | 0 | 0 MEDIASTINAL LYMPH NODE |
| | | | | I | 4 TUMENTIA |
| | | | | IIA | 6 CORONARY ARTERY CALCIFICATION |
| | | | | IIB | 8 CALCIFICATION |
| | | | | III | 9 EMPHYSEMA |
| | | | | IV | 10 |
| | | BENIGN TUMOR | 5 | | 2 |
| | | PNEUMONIA | 5 | (MEASURED LUNG) ~1/3 | 2 |
| | | | | (MEASURED LUNG) 1/3~2/3 | 6 |
| | | | | (MEASURED LUNG) ~2/3 | 10 |
| | THORACIC AORTA | AORTIC ANEURYSM | 8 | 4cm | 2 AORTIC CALCIFICATION |
| | | | | 5cm | 4 |
| | | | | 8cm | 6 |
| | | | | 8cm | 8 |
| | | | | 10cm~ | 10 |
| | MEDIASTINAL LYMPH NODE | MEDIASTINAL LYMPH NODE TUMENTIA | 10 | 1cm~ | 10 |

601

EXAMPLE OF MEDICAL KNOWLEDGE DATA WHEN EXAMINATION PURPOSE IS CLOSE EXAMINATION/FOLLOW-UP

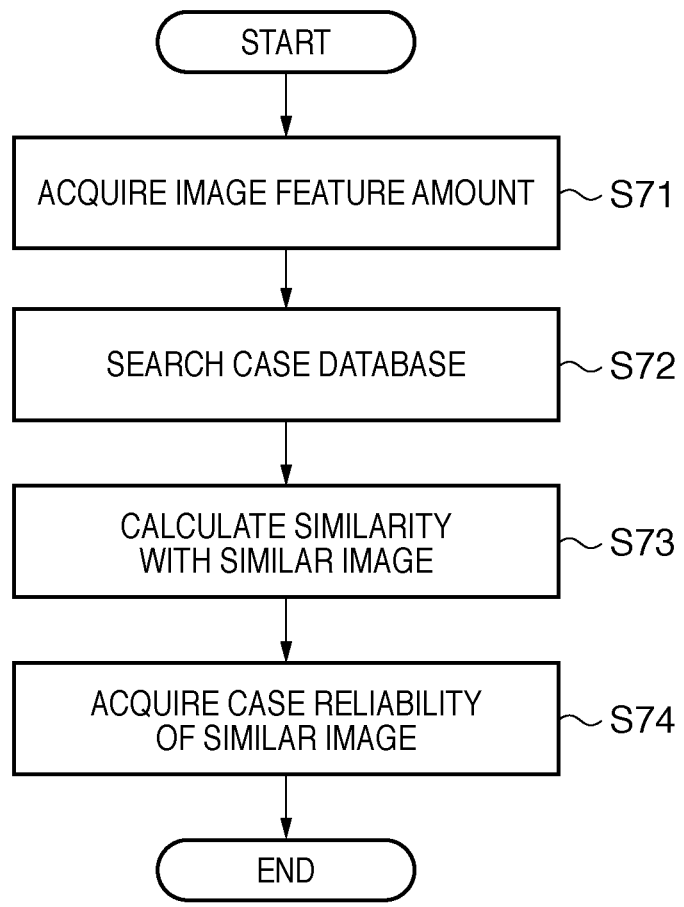

DIAGNOSIS SUPPORT APPARATUS, METHOD OF CONTROLLING DIAGNOSIS SUPPORT APPARATUS, AND PROGRAM THEREFOR

CROSS REFERENCE TO RELATED APPLICATIONS

This application is a National Stage filing of PCT application No. PCT/JP2008/066238 filed on Sep. 9, 2008 which claims priority from Japanese Patent Application No. 2007-271300 filed on Oct. 18, 2007, the disclosures of which are hereby incorporated by reference herein in their entirety.

TECHNICAL FIELD

The present invention relates to a medical diagnosis support system which performs computer processing of data obtained from an object to be examined and presents obtained diagnostic information.

BACKGROUND ART

In the medical field, a doctor displays a medical image obtained by imaging a patient on a monitor, interprets the displayed medical image, and observes the state of a lesion and its change with time. The following are available as apparatuses designed to generate this type of medical images:
 Computed Radiography (CR)
 Computed Tomography (CT)
 Magnetic Resonance Imaging (MRI)
 Ultrasound System (US)

With the purpose of reducing the load of such interpretation on a doctor, there has been developed a diagnosis support apparatus which automatically detects a lesion or the like by digitizing a medical image and performing image analysis, and performs computer-aided diagnosis (Kawata, Niki, and Ohmatsu, "Curvature Based Internal Structure Analysis of Pulmonary Nodules Using Thoracic 3-D CT Images", the transactions of the Institute of Electronics, Information and Communication Engineers D-II, Vol. J83-D-II, No. 1, pp. 209-218, January 2000).

Computer-Aided Diagnosis will be referred to as CAD hereinafter. CAD is designed to automatically detect an abnormal shadow candidate as a lesion. In this abnormal shadow detection processing, performing computer processing of image data representing a radiographic image will detect an abnormal tumor shadow indicating a cancer or the like, a high-density minute calcified shadow, or the like. Presenting this detection result can reduce the load of interpretation on a doctor and improve the accuracy of the interpretation result.

The Japanese Society of CT Screening (NPO) provides determination criteria and follow-up guidelines for lung cancer CT screening by single slice helical CT to help doctors avoid misdiagnosis in interpretation.

A diagnosis support apparatus to perform computer support diagnosis calculates an abnormal shadow candidate always considering the balance between "sensitivity" and "misdiagnosis detection", which contradict each other (Japanese Patent No. 3417595).

For example, increasing "sensitivity" as a parameter for adjusting the number of tumor shadow candidates to be extracted will increase the number of times of "misdiagnosis detection", that is, extraction of shadows which are not actually tumors.

As described above, increasing "sensitivity" will reduce oversight but increase "misdiagnosis detection". A false positive lesion candidate is called an FP (false positive).
Patent reference 1: Japanese Patent No. 3417595
Non-patent reference 1: Kawata, Niki, and Ohmatsu, "Curvature Based Internal Structure Analysis of Pulmonary Nodules Using Thoracic 3-D CT Images", the transactions of the Institute of Electronics, Information and Communication Engineers D-II, Vol. J83-D-II, No. 1, pp. 209-218, January 2000
Non-patent reference 2: determination criteria and follow-up guidelines for lung cancer CT screening by single slice helical CT, "The Japanese Society of CT Screening (NPO)"

DISCLOSURE OF INVENTION

Problems that the Invention is to Solve

The computer-aided diagnosis system disclosed in Japanese Patent No. 3417595 performs computer-aided diagnosis by using only data obtained from an object to be examined. That is, this system has given no consideration to the examination history of an object and has not met the requirement for more accurate diagnosis.

In consideration of the above situation, the present invention provides a mechanism for obtaining diagnostic information by computer processing with consideration also given to the examination history of an object.

Means of Solving the Problems

In order to achieve the above object, a diagnosis support apparatus according to an aspect of the present invention comprises diagnosis support processing means for processing data obtained from an object to extract diagnosis support information, storage means for storing an examination history of the object, and changing means for changing a processing method in the diagnosis support processing means in accordance with the examination history of the object stored in the storage means.

Effects of the Invention

The arrangement of the present invention can provide a mechanism for providing diagnostic information by computer processing with consideration given to the examination history of an object.

Other features and advantages of the present invention will be apparent from the following description taken in conjunction with the accompanying drawings, in which like reference characters designate the same or similar parts throughout the figures thereof.

BRIEF DESCRIPTION OF DRAWINGS

FIG. 6 is a view showing an example of data stored in a medical knowledge database in the diagnosis support apparatus; and FIG. 7 is a flowchart showing a processing sequence for searching for a similar image of a case in the diagnosis support apparatus.

BEST MODE FOR CARRYING OUT THE INVENTION

Figure 1:
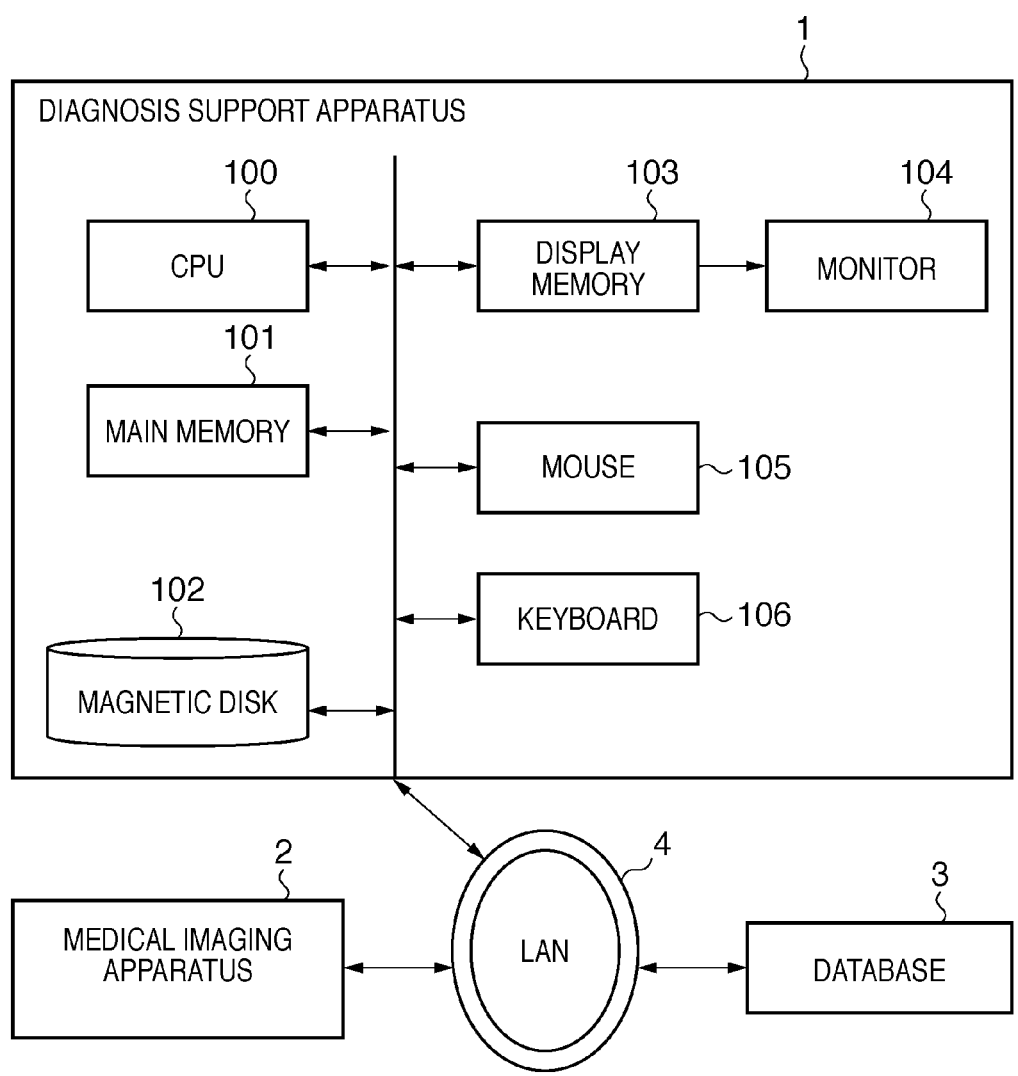
FIG. 1 is a block diagram showing the configuration of a diagnosis support apparatus system.

The preferred embodiments of the present invention will be exemplarily described in detail below with reference to the accompanying drawings. Note however that the constituent elements described in the embodiments are merely examples, and the scope of the present invention is not limited to them.

First Embodiment

A CPU 100 mainly controls the operation of each constituent element of a diagnosis support apparatus 1. A main memory 101 stores control programs to be executed by the CPU 100 or provides a work area when the CPU 100 executes a program. A magnetic disk 102 stores an operating system (OS), device drives for peripheral devices, various kinds of application software including programs for executing, for example, diagnosis support processing (to be described later), and the like. A display memory 103 temporarily stores display data for a monitor 104. The monitor 104 is, for example, a CRT monitor or a liquid crystal monitor, and displays images based on data from the display memory 103. A mouse 105 and a keyboard 106 are operated by the user to perform pointing input operation and input characters and the like. The respective constituent elements described above are connected to each other via a common bus 107 so as to be communicable with each other.

In this embodiment, the diagnosis support apparatus 1 can read out image data and the like from a database 3 via a LAN 4. Alternatively, it suffices to connect storage devices such as an FDD, CD-RW drive, MO drive, and ZIP drive to the diagnosis support apparatus 1 to allow it to read image data and the like from the drives. In addition, the diagnosis support apparatus can directly acquire medical images and the like from a medical imaging apparatus 2 via the LAN 4.

An example of the arrangement of the diagnosis support apparatus 1 will be described with reference to FIG. 2.

Figure 2:
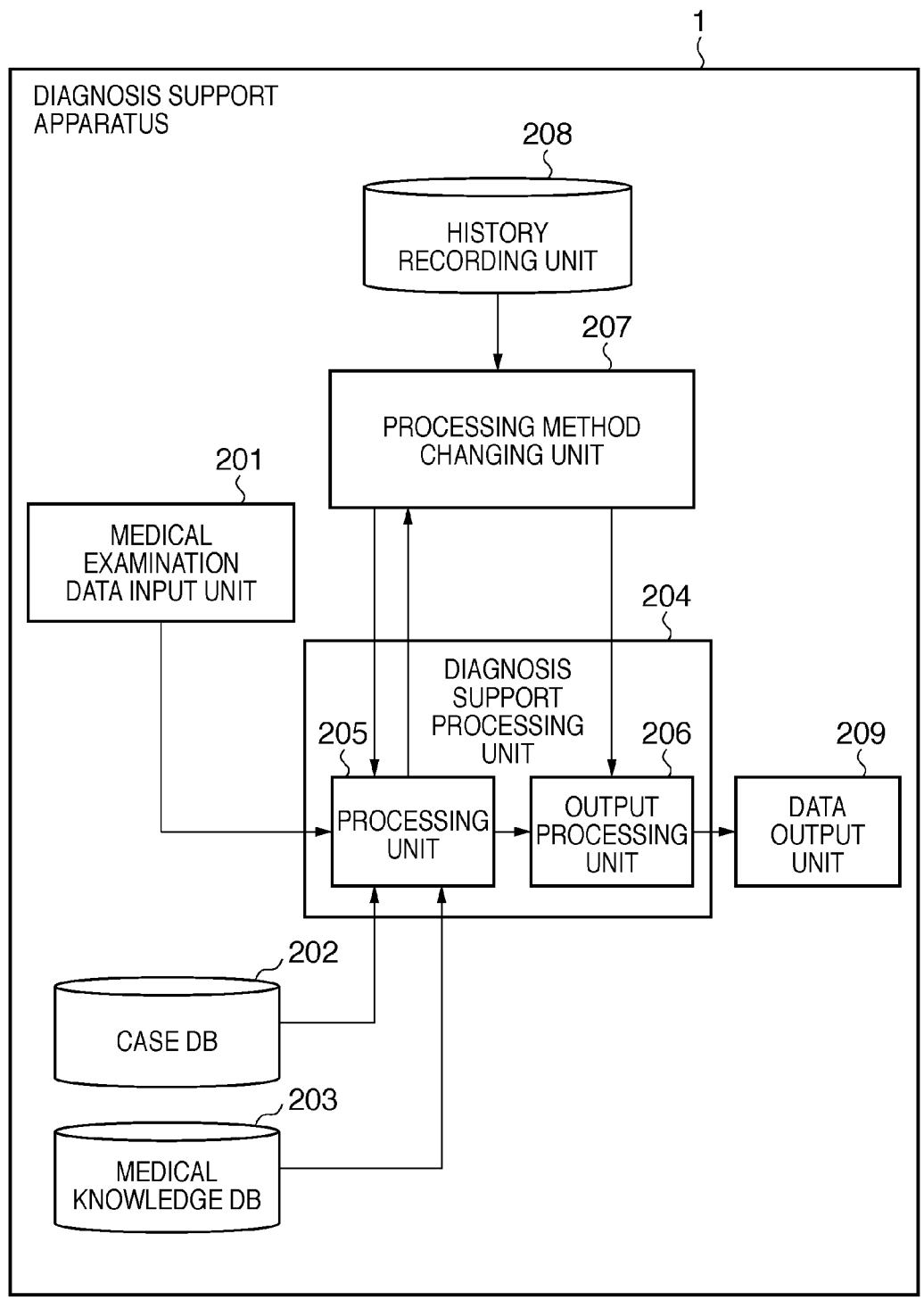
FIG. 2 is a block diagram showing the functional arrangement of a diagnosis support apparatus.

Referring to FIG. 2, the diagnosis support apparatus 1 includes a medical examination data input unit 201, a case database 202, a medical knowledge database 203, a diagnosis support processing unit 204 as a diagnosis support processing means, a processing method changing unit 207, a history recording unit 208 as a storage means, and a data output unit 209.

The medical examination data input unit 201 acquires data concerning an object to be examined, for example, image data and measurement data such as an electrocardiogram, brain wave data, and leukocyte count, which are acquired from, for example, an X-ray imaging apparatus, CT apparatus, MR apparatus, and ultrasonic or sound diagnosis apparatus.

The medical examination data input unit may also be configured to input medical examination data including information associated with the acquisition of lesion candidates, for example, medical record information. In this case, this unit may be configured to either allow a user to directly input these data or read them from various types of storage media such as an FDD, CD-RW drive, MO drive, and ZIP drive on which information is recorded. Alternatively, the unit may be configured to be connected to a database storing these data via a LAN so as to receive them therefrom.

The case database 202 stores image data captured by the medical imaging apparatus 2, numerical data including electrocardiograms and leukocyte counts, and text data such as medical records on objects to be examined. Each case data can include data processing result values and a confirmed diagnosis result obtained by the diagnosis support apparatus. It is possible to use these pieces of information for an analogous case search.

In addition, the case database stores templates classified into categories used for recognition/identification processing. Such a template is used for pattern recognition processing to determine the type of lesion (e.g., malignant or benign). In addition, when a lesion is to be extracted, the template is used to extract a region which is a lesion based on the similarity (e.g., a correlation value) with data extracted from an object.

The medical knowledge database 203 stores diagnosis criteria for lesion regions and information of diseases as examination targets including metastatic lesions and complications. This database may also store data including a diagnosis sequence such as a sequence for checking, upon detection of a primary lesion, the presence/absence of an associated disease.

The diagnosis support processing unit 204 acquires information for supporting diagnosis from data obtained from the object.

When processing image data, a processing unit 205 acquires information concerning a lesion from the data acquired from the object. This unit extracts, for example, a lesion such as a candidate region of a tumor shadow or a candidate region of a calculus.

When acquiring a lesion candidate as a candidate of a lesion, this unit can also compare similarities with past case data by referring to the case database 202. In this case, the processing unit 205 calculates a feature amount from an image, and acquires a lesion candidate from the coincidence of the feature amount for each case stored in the case database 202.

This processing unit may refer to data concerning diagnosis criteria and diagnosis sequences stored in the medical knowledge database 203. Consider, for example, a diagnosis criterion when CT images are used. In this case, a CT value range corresponding to a lesion is set. It is highly possible that a lesion exists in the range. A lesion is therefore extracted from the range. In addition, for a diagnosis sequence, a diagnosis trial by a doctor is grammaticalized as a flowchart. For example, in the case of two-dimensional image data, a processing sequence required for the extraction of a region of interest from an object and computer processing such as the digitization of texture features in the region of interest is grammaticalized in accordance with the way of thinking of a doctor.

Note that the processing targets of the processing unit 205 are not limited to image data. For example, the processing targets include measurement data other than images concerning an object or medical record data. The processing unit can be configured to acquire lesion candidates based on these data.

If image data is a target, an output processing unit 206 acquires information for supporting diagnosis of the likelihood of a lesion or the like with respect to a lesion candidate extracted by the processing unit 205. In the case of measurement data, the output processing unit directly analyzes data obtained from the object and acquires and outputs information for supporting diagnosis.

The history recording unit 208 records diagnosis history information concerning the object. As diagnosis history information, this unit records examination methods performed in the past, diagnosis results obtained by the methods, and the like. The unit also stores an onset probability estimated in the past, a next diagnosis period corresponding to the onset probability, and the like.

As an examination method, this unit also records the purpose information of an examination such as screening, close examination, or follow-up of a lesion.

The processing method changing unit 207 determines processing methods for the processing unit 204 and the output processing unit 205 in accordance with the history information of the object which is obtained from the history recording unit 208.

The data output unit 209 outputs the data of a lesion candidate obtained by the processing unit 205 and the determination information of the lesion candidate obtained by the output processing unit 206 in a designated format.

Figure 3:
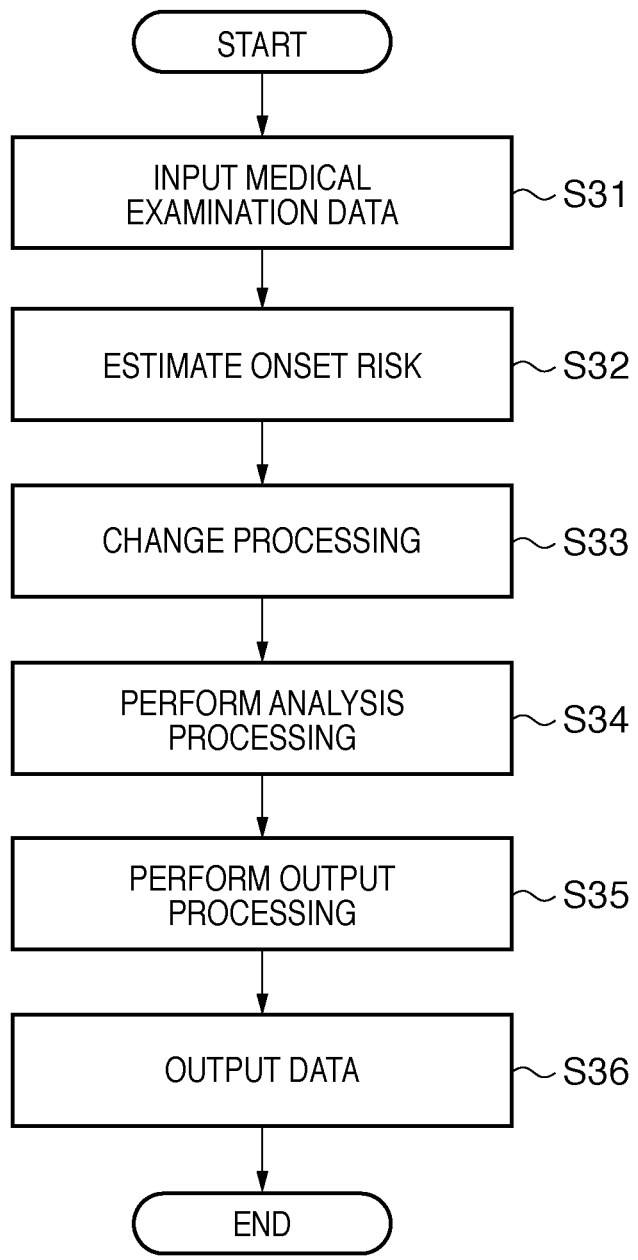
FIG. 3 is a flowchart showing a processing sequence in the diagnosis support apparatus.

The manner of how the CPU 100 controls the diagnosis support apparatus 1 will be described next with reference to the flowchart of FIG. 3.

In step S31, the CPU 100 inputs medical examination data from the medical examination data input unit 201 to the diagnosis support apparatus 1.

In addition, since different lesion detection criteria and different lesion detection sequences are used to acquire lesion candidates in accordance with examination purposes, the CPU acquires the examination history of the object (e.g., the history of examination from the day of previous imaging to the day of examination) and the information of an examination purpose from the history recording unit 208.

In step S32, the processing method changing unit 207 estimates a current onset probability under the control of the CPU 100 in accordance with the history information of the object recorded on the history recording unit 208. In this case, the onset probability is the probability of the onset of a lesion. It also refers to the probability at which a lesion will change from benignity to malignancy.

A symptomatic change that can occur in accordance with the lapse of time after examination of the object is stored as probabilistically significant information according to past medical findings. Therefore, a symptomatic change can be predicted within a probabilistically significant range in accordance with information in the course of time. That is, it is possible to predict the symptomatic change of the object within a probabilistically significant range in accordance with the examination history of the object.

When estimating an onset probability, the CPU calculates the progress degree of a lesion candidate by using the past and current examination data of the object, the time intervals of diagnosis such as a checkup count, history information such as an onset probability estimated by a past checkup, lesion candidate data as an image processing result, and the like which are recorded on the history recording unit 208.

For example, the CPU predicts the current size of a lesion (a tumor or calculus) of the object from the information of the lesion recorded on the history recording unit 208. This prediction is performed by using the past size and growth rate of the lesion. In this case, the CPU uses, as a growth rate, a statistic recorded on the medical knowledge database 203 by using the past size and type of a lesion. In addition, if a change in the size of a lesion is recorded on the history recording unit 208, it is possible to obtain the size of the lesion at a given time point in the past. Furthermore, if, for example, the predicted size is 5 mm or more, the CPU determines that the onset probability is high. In this case, the onset probability is the probability at which the extracted lesion candidate is malignant. The processing method changing unit 207 changes the size of a lesion to be extracted by the processing unit 205 in accordance with this onset probability as well. If this onset probability is high, since there is a possibility that a new lesion will develop, the processing unit extracts lesions of sizes in the entire range. In addition, in some cases, the processing function is changed in accordance with the size of a lesion.

If it is determined from the history of the object recorded on the history recording unit 208 that the object is taking the first medical examination, the processing unit extracts lesions of sizes in the entire range, considering that the onset probabilities are high.

If the history of the object recorded on the history recording unit 208 has no history of extraction of a lesion, the onset probability changes in accordance with the lapse of time after the previous diagnosis. If not much time has elapsed since the previous examination, the probability of the development of a large lesion significantly decreases. For this reason, the CPU changes a parameter in the processing method changing unit 207 to prevent the processing unit 205 from extracting a large lesion, considering that the onset probability is low. This can perform extraction in accordance with a specific size, and hence decreases the false positive rate of lesions extracted by the processing unit 205.

In this manner, the processing method changing unit 207 changes the processing method used by the diagnosis support processing unit 204 based on the history of the object recorded on the history recording unit 208.

The ways of changing the processing method used by the diagnosis support processing unit 204 include, for example, the following methods: adjusting the probability distribution of reliability; adjusting a threshold for the probability of recognition of abnormality; changing a parameter of a recognition function such as a Bayesian discriminator; and moving an interface in a feature space in a discriminator. In addition, it is possible to change the determination algorithm itself. Selecting a support vector machine, Bayesian discriminator, neural network, or AdaBoost, other than a linear discriminant function, is also equivalent to changing the processing method.

For example, the following settings are made as onset probabilities: onset probability=1.0: which is an onset probability set when no onset probability can be estimated or is regarded as a default, in which state, the parameter of a discriminator which is used as a default is used; onset probability=0.9: to which the discriminator is set by decreasing the sensitivity of the discriminator such that false positives appear at a rate of 90% of that in the default state when the onset probability is low; and onset probability=1.1: to which the discriminator is set by increasing the sensitivity of the discriminator such that false positives appear at a rate of 110% of that in the default state when the onset probability is high. The above settings are merely an example, and do not limit this embodiment.

In step S33, the processing unit 205 extracts a lesion candidate, under the control of the CPU 100, by the processing method determined in step S32. In this case, the CPU obtains lesion candidate data such as a reliability indicating the likelihood of a lesion and the progress degree of the lesion from the feature amount calculated from the lesion candidate by using the information of a diagnosis criterion stored in the medical knowledge database 203. In this case, the reliability indicates, for example, the likelihood of a lesion based on a correlation value with the feature amount obtained from a past lesion and the like.

In the case of a chest CT image, the processing unit 205 segments the image into regions such as a lung field region, diaphragm region, bronchus region, pulmonary artery region, and pulmonary vein region, and classifies the lung field into a superior lobe segment, median lobe segment, and inferior lobe segment. As an example of a method of detecting an organ region from a medical image, a level set method which is a kind of dynamic contour method will be described below. The level set method defines a level set function which is one dimension higher than a detection target region, and regards a region which is to be extracted as its zero contour line. Updating this function based on the following evolution equation called a level set equation will control a contour and detect a region.

$$\phi t + F|\nabla \phi| = 0$$

where $\phi t$ represents the value obtained by calculating the first derivative of the level set function, F represents the growth rate of the contour, and $|\nabla \phi|$ represents the absolute value of the gradient of the level set function.

In this manner, an organ region can be detected from the medical image. The detection of an organ region has been described above by exemplifying the level set method. However, as a region detection method, the following is available: a method based on threshold processing, region growing, dynamic contour method, clustering, graph minimum cut algorithm, or the like. An organ region is detected by using one of these methods or other techniques.

These methods can be switched and used in accordance with the region to be detected. It suffices to perform region detection by using a probability atlas, a human body shape model, and the like as prior knowledge as well as an image feature amount.

The following are available as methods of detecting an abnormality such as a lung field tumor from an organ region: filter processing for detecting an abnormality, pattern matching, abnormality detection using a discriminator, and difference detection processing by registration between, for example, past images or average shape images and diagnosis images. In addition, image feature amounts for specifying a lung field tumor include a shape index and curvedness obtained from the CT value of each pixel inside the tumor and a three-dimensional curvature (a Gaussian curvature, average curvature, or principal curvature).

A lesion candidate is detected by using one of the above techniques or other techniques.

In step S35, the CPU 100 causes the output processing unit 206 to evaluate the lesion candidate detected by the processing unit 205 in accordance with the processing method determined by the processing method changing unit 207.

In order to perform disease classification and benign/malignant discrimination of abnormalities, malignancy probabilities (probability values) are subjected to disease classification and benign/malignant discrimination using a discriminator using a discrimination method (e.g., a linear discriminant function, support vector machine, AdaBoost, Bayesian discriminator, or neural network). The method to be used for the abnormality detection, disease classification, and benign/malignant discrimination is not limited to the above technique.

It is further possible to give more consideration to a feature amount itself or replacing it as well as changing the weight of a feature amount used in the discriminator.

The following is a case in which benign/malignant discrimination of a lung field tumor candidate is performed by applying the feature amount extracted from an X-ray CT image to the following linear discriminant function. That is, lesion candidates are classified into true lesions and false positives.

$$f(x) = \left\{ x - \frac{1}{2}(m_1 + m_2) \right\}^t \sum_w^{-1} (m_1 - m_2) \qquad \text{[Mathematical 1]}$$

where x represents a feature vector of one pattern, m1 and m2 represent the average vectors of classes 1 and 2, and $\Sigma W$ represents a within-class covariance matrix. The value of a linear discriminant function f is regarded as a discriminant score. When this value is negative, the lesion candidate is classified into class 1 (benign). When the value is positive, the lesion candidate is classified into class 2 (malignant). The CPU then changes the parameter $\Sigma W$ of the above linear discriminant function in accordance with the onset probability. That is, when determining that the onset probability is high, the CPU sets $\Sigma W$ so as to allow f to output more positive values. When determining that the onset probability is low, the CPU sets $\Sigma W$ so as to allow f to output more negative values.

That is, upon estimating that the onset probability is high, the CPU makes more lesion candidates attract attention. That is, the CPU increases the sensitivity of the output processing unit 206. In contrast, upon estimating that the onset probability is low, in order to reduce the number of false positive lesion candidates, the CPU decreases the sensitivity to present fewer lesion candidates which are not relatively important.

It suffices to perform the processing in the output processing unit 206 in conjunction with the sensitivity of the processing unit 205 or independently. That is, it is possible to extract many tumor shadows by maximizing the sensitivity of the processing unit 205 and change the threshold in the output processing unit 206 so as to decrease the number of false positive lesion candidates. Alternatively, it is possible to perform this processing in conjunction with the sensitivity of the processing unit 205.

In step S36, the CPU narrows down the lesion candidate data detected in step S32 to the lesion candidate data which are determined in step S35 to satisfy the criterion of recognition of a lesion, and outputs them.

In this case, the data output unit 209 converts the above data into output data corresponding to an output destination under the control of the CPU 100. The output destination includes a sheet, a storage device such as a memory or a hard disk, and a monitor.

Figure 4:
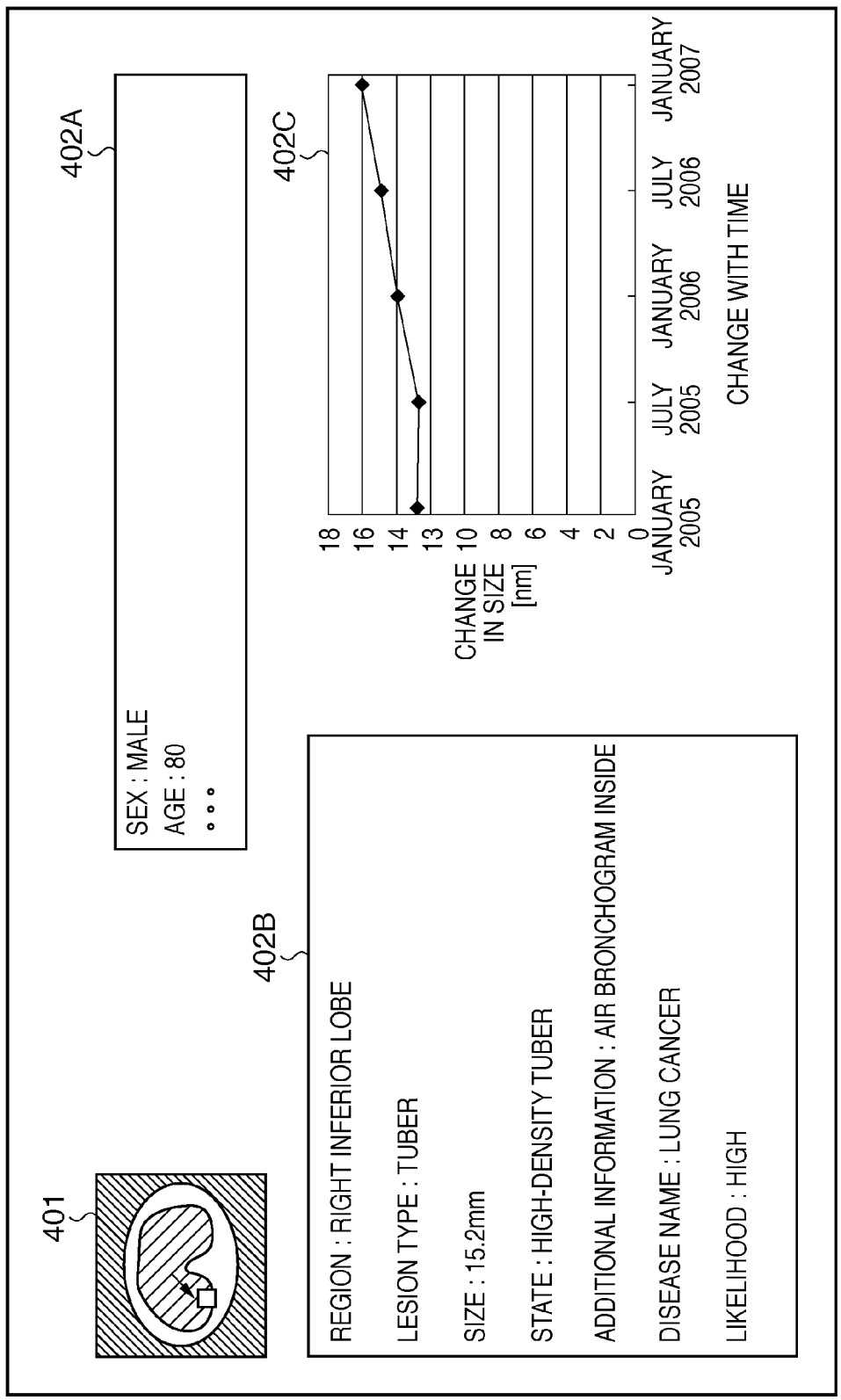
FIG. 4 is a view showing an output example from the diagnosis support apparatus.

FIG. 4 shows an output example of lesion candidate data. A mark indicating a lesion candidate is displayed on medical examination data. Image feature amounts and patient attribute/time-varying data are displayed next to the medical examination data. In addition, when lesion candidate data is to be output to a display device such as a monitor, it suffices to display the data in a popup form or in another window.

A method of predicting the size of a lesion candidate in step S33 which is executed by the processing method changing unit 207 described above will be described next with reference to FIG. 5. The history recording unit 208 records a predicted size as history information of the object to allow the information to be used for the next diagnosis processing or the determination of a next diagnosis timing.

A prediction method based on the size and growth rate of a tumor as an example will be described below. In this case, the longest diameter is used as the size of a tumor.

In step S51, the processing method changing unit acquires the tumor detected in step S32 from the current chest image data, and calculates the longest diameter of the tumor.

In step S52, the processing method changing unit checks whether the past chest image data or past diagnosis report of the object includes a description of a lesion corresponding to the tumor acquired in step S51. If there is a description of the lesion in the past, the process advances to step S53.

If the lesion candidate detected in step S51 is detected for the first time by this checkup, the process advances to step S55.

In step S53, the processing method changing unit acquires the past information of the tumor from the history recording unit 208. The information to be acquired includes the size (the longest diameter in this case), diagnosis on the case, and the reliability of the diagnosis. The diagnosis support processing unit 204 may calculate this information if it is not described in the past diagnosis report.

In step S54, the processing method changing unit calculates a growth rate from the current and past longest diameter values of the corresponding tumor and the time period from the past checkup according to the following equation. Although the following equation is used as an example in this case, the present invention is not limited to this. For example, it suffices to use another method of calculating a growth rate, which is accepted in the medical field, like a method using a mathematical expression additionally including a weight and an adjustment term in accordance with the region to be processed.

$$VC=(MRpresent-MRpast)/t$$

where VC is a growth rate, MRpresent is the current longest diameter value of the tumor, MRpast is the longest diameter value of the corresponding tumor at the time of a past examination, and t is the time elapsed since the past examination.

In step S55, if there is no past information of the detected tumor, the processing method changing unit uses the value of the growth rate of the tumor which is empirically known in the medical field. Obviously, it suffices to use a mathematical expression or method of deriving the growth rate of the tumor in accordance with other examination data of the object or information such as a past case.

In step S56, the processing method changing unit acquires a next scheduled checkup date (next checkup timing) for the object which is recorded on the history recording unit 208, and estimates the size of the tumor at the time of the next checkup based on the current size of the tumor, the growth rate, and the number of days to the next checkup. For example, as a method of estimating the size of a tumor, the following equation is available. However, the method is not limited to the equation, and the size of the tumor may be estimated in accordance with empirical values summarized in a table as medical knowledge.

$$MRfuture=MRpresent+VC*tf$$

where MRfuture is the prediction of the size of the tumor at the time of the next scheduled checkup, and tf is the time to the next scheduled checkup.

In step S57, the processing method changing unit estimates an onset probability by comparing the prediction of the size of the tumor at the time of the next checkup, which is calculated in step S56, with a medical guideline. If, for example, the size of the tumor is predicted to be less than 5 mm, it can be determined that the onset probability is low. If the size of the tumor is predicted to be 10 mm or more, it can be determined that the onset probability is high.

Figure 5:
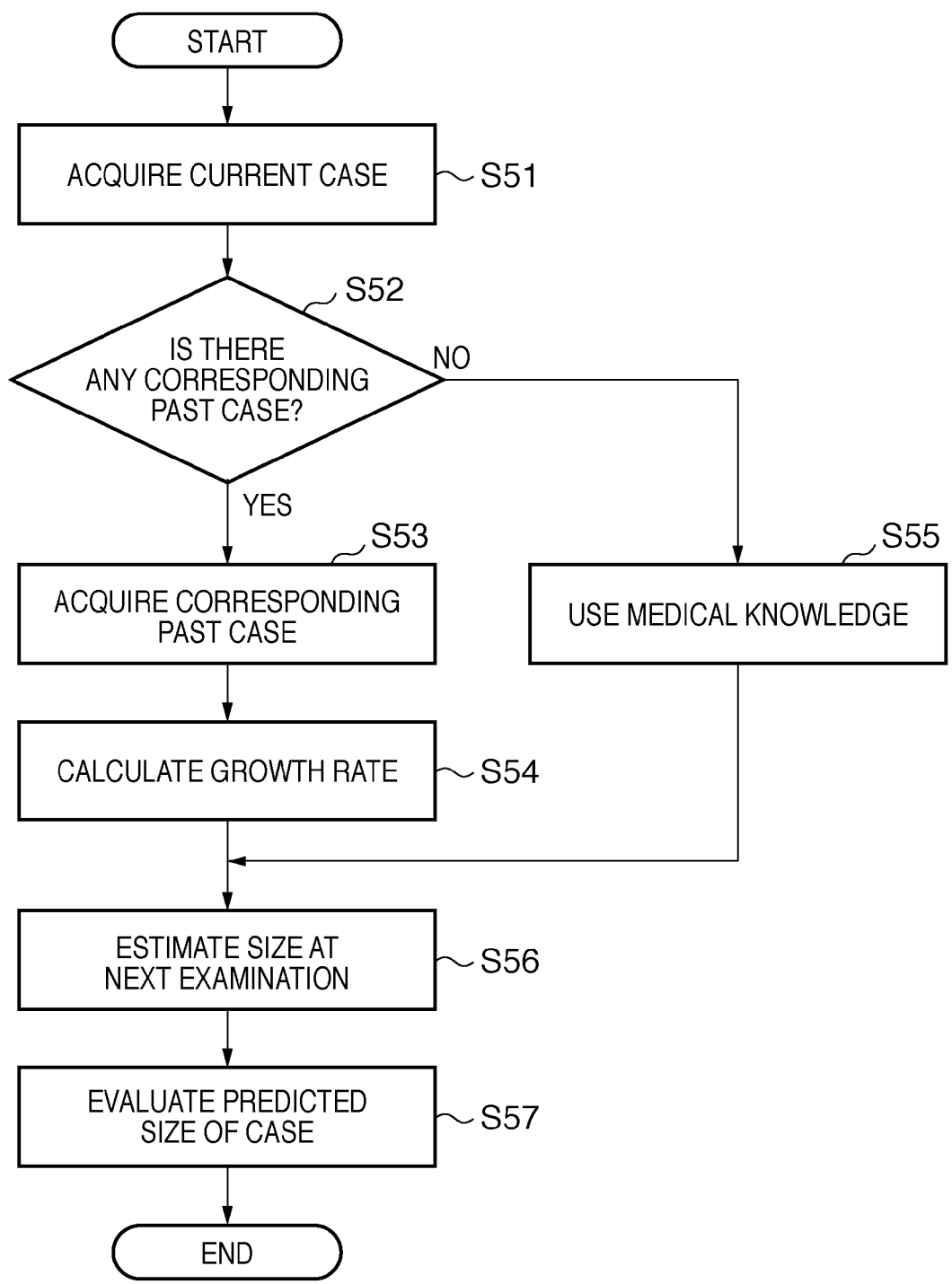
FIG. 5 is a flowchart showing a processing sequence for calculating the size of a lesion candidate in the diagnosis support apparatus.

With the above processing shown in FIG. 5, it is possible to predict the size of a lesion at the time of a next checkup. Using this information allows the processing method changing unit 207 to estimate an onset probability.

In the above description, the size of a tumor is expressed by its longest diameter. However, the present invention is not limited to this as long as the size and growth rate of a tumor can be expressed. For example, the volume of the tumor can be used.

As a method of estimating an onset probability in step S32, an example using medical importances will be described next.

The processing method changing unit 207 estimates an onset probability in accordance with the medical importance of a lesion candidate acquired by the processing unit 205. Alternatively, it is possible to estimate an onset probability in accordance with an interval change in the medical importance of a lesion candidate.

A medical importance I calculated by the processing method changing unit 207 will be described below.

The medical importance I can be defined as follows:

$$I=A*B*C$$

where

A: important morbidity (relative disease severity among different kinds of diseases)

B: progress degree (stage) (disease severity within same kind of disease)

C: associated morbidity

If, for example, the processing unit 205 is to detect a plurality of kinds of diseases, the associated morbidity C is set for each lesion in accordance with the examination purpose as follows. That is $$C = \begin{cases} 1 \text{ (examination target (primary) disease)} \\ 0.5 \text{ (metastasis} \cdot \text{complication disease candidate)} \\ 1 \text{ (others)} \end{cases} \quad \text{[Mathematical 2]}$$

FIG. 6 shows examples of the important morbidity A and the progress degree B.

Assume that in the case of follow-up of a lung cancer, the processing unit 205 has detected one malignant tumor (stage 0) in the lung field as a lesion candidate. In this case, a medical importance IC concerning the malignant tumor is obtained as follows:

$$IC=10*2*1=20$$

Subsequently, in order to estimate an onset probability, the processing method changing unit compares this medical importance with the medical importance of a corresponding lesion of the patient in the past. If the history recording unit 208 indicates that it was determined in a past examination that the same tumor was determined as a benign tumor, the processing method changing unit obtains a past medical importance IP of the tumor as follows:

$$IP=5*2*1=10$$

That is, since the medical importance has increased within a given time period, it is estimated that the onset probability is high. Alternatively, even if the medical importance has not changed, it is estimated that the onset probability is high, when the medical importance is kept at a value equal to or more than a given value for a predetermined time period.

Furthermore, in order to estimate an onset probability based on changes in medical importance described above, it is also possible to use a table (medical importances, changes in medical importance, and time periods) formed from cases collected by medical researches.

Note that the contents of medical importances described above are only an example, and are not limited by the definition in this embodiment. For example, it suffices to give consideration to examination purpose information concerning screening, close examination, and follow-up when estimating an onset probability based on a medical importance.

A method of estimating an onset probability by using the probability (called a certainty factor in some cases) of a lesion candidate being a lesion will be described next.

In this case, a method of calculating the probability of a lesion candidate being a lesion includes detecting a lesion candidate by a similar image search. A processing sequence for a similar image search will be described with reference to FIG. 7.

In step S71, the processing unit 205 calculates image feature amounts by processing medical examination data. Image feature amounts include, for example, the luminance distribution obtained from general image processing and the 2D or 3D feature amount of a region of interest in an image. Alternatively, it suffices to use a "shape index" value and a "curvedness" value.

In step S72, a case represented by an image having a feature amount similar to the feature amount of the image calculated by the processing unit 205 is acquired by searching the case database 202 using the calculated feature amount. In addition, cases are stored in advance in association with feature amounts, and the information of a case is acquired from a feature amount with a case.

In step S73, found images are arranged in decreasing order of similarity of feature amounts, and the similarities of the images are calculated in decreasing order of similarity. In this case, a value used as an example of similarity is the inner product value of the normalized feature vectors of a reference image and a similar image in a feature space used for a search. That is, in the feature space, the closer the feature amounts of a reference image and similar image, the more similar the two images. Note that the method of calculating similarities described above is merely an example, and the present invention is not limited to the method in this embodiment.

In step S74, a finding associated with a case represented by the found image or the feature amount obtained from the image is acquired. Elements A, B, and C for obtaining the above medical importances are respectively attached to findings. For example, cancers include cancers with high progress rates and highly metastatic cancers, which are malignant and high in medical importance. In addition, the certainty factor of a selected case is acquired when it is selected by pattern matching. In this case, a certainty factor indicates the probability of a case being malignant when a plurality of doctors diagnose the case. In addition, it suffices to set a success ratio (the probability that a finding from a doctor coincides with an output finding from a discriminant function) obtained when a case is determined by the discriminant function as a certainty factor which is a statistic. A change T in lesion similarity is defined based on the obtained similarity and the certainty factor of the case as follows:

$$T = S_{present} * C_{present} - S_{past} * C_{past}$$

where Spresent is the similarity obtained by the current examination, Cpresent is the certainty factor obtained by the current examination, Spast is the similarity of a corresponding case of the patient in the past which is recorded on the history recording unit, and Cpast is the certainty factor of the corresponding case of the patient in the past which is recorded on the history recording unit. If the change T described above has increased within a given time period, it is estimated that the onset probability is high.

It is also possible to use, for example, a support vector machine or another discriminator used for pattern recognition, other than the above method, to calculate the probability of a lesion candidate. That is, the calculation method to be used is not limited to the above method using similarities.

As described above, according to the first embodiment, considering the history of a patient can adjust the sensitivity of diagnosis support and reduce the load of interpretation on a doctor. This makes it possible to reduce the load on the patient because oversight or unnecessary biopsies are reduced.

Second Embodiment

The first embodiment has exemplified the case in which the sensitivity of diagnosis support is adjusted based on the onset probability of a patient. However, it is assumed that examination data obtained from a medical examination data acquisition apparatus is the one obtained with standard parameters.

The second embodiment will describe a way of changing an acquisition parameter in a medical examination data acquisition apparatus in accordance with the onset probability of a patient.

Although it depends on the type of medical examination data acquisition apparatus, increasing the sharpness of acquired examination data may increase the load (the invasiveness of examination) on the patient. In the case of an X-ray CT apparatus, for example, suppressing the exposure dose of the patient by decreasing the voltage or current amount of an X-ray tube will increase noise in an obtained slice image. As a method of reducing the overall exposure dose of the patient without reducing the dose of the X-ray tube (X-ray source), it is conceivable to increase the moving speed of the bed. However, the intervals between slice images increase, and hence there is a possibility that a lesion may not be depicted, falling outside a slice image.

This embodiment changes an acquisition parameter in the medical examination data acquisition apparatus in accordance with the onset probability of a patient which is calculated in the first embodiment.

In the X-ray CT apparatus, when it is determined that the onset probability is low, the dose of the X-ray source is reduced or the slice intervals are increased. If it is determined that the onset probability is high, the X-ray dose is increased to obtain sharper medical images or the slice intervals are decreased.

If the onset probability at a specific region is high, it is possible to image only the region with high sharpness or examine other regions by a method with a less load.

It is also conceivable to change the calculation algorithm for examination data. In the case of an X-ray CT apparatus, since the reconstruction algorithm can be changed, an algorithm that can obtain sharper images may be selected, even if it is slow, when the onset probability is high, whereas when the onset probability is low, a fast algorithm may be selected.

In addition, it suffices to adjust an acquisition parameter such as the amount of contrast medium for MRI. Furthermore, an onset probability can be used to select a medical examination data acquisition apparatus. For example, if it is determined that the onset probability is high, it is possible to perform examination more suitable for the case (e.g., PET).

As described above, according to the second embodiment, adjusting an acquisition parameter in the examination apparatus in accordance with the onset probability estimated from the history of a patient can acquire more detailed features of the case.

Third Embodiment

The second embodiment has described that it is possible to detect a lesion with a high onset probability more accurately by changing an acquisition parameter in the medical examination data acquisition apparatus in accordance with the onset probability of a patient.

Note that final diagnosis is performed by a doctor qualified to perform diagnosis such as an interpreting doctor or an attending physician. In order to confirm the diagnosis, therefore, the image diagnosis support apparatus needs to present not only the information of a lesion candidate but also the information of a criterion for regarding a lesion as a candidate.

In this case, an image diagnosis support apparatus 1 presents the doctor the onset probability of a patient, a change in sensitivity parameter (a changed parameter, its value, or a changed algorithm), and the reason and ground of the change, together with the related information of the detected lesion candidate and an interpretation report. As a result output method, it suffices to display the result on the screen of a terminal used for interpretation as well as an interpretation report as a paper medium or to use other presentation methods.

As described above, according to the third embodiment, presenting the onset probability of a sensitivity parameter and change information together with a diagnosis report makes it possible to perform more accurate diagnosis. In addition, a doctor can comprehend the health of a patient better and manage patient information.

Other Embodiments

Obviously, the object of the present invention is also implemented by supplying a computer-readable storage medium storing programs for implementing the functions of the above embodiments to a system or apparatus, and causing the computer (or a CPU or an MPU) of the system or apparatus to read out and execute the program codes stored in the storage medium.

In this case, the program codes read out from the storage medium implement the functions of the above embodiments by themselves, and the storage medium storing the program codes constitutes the present invention.

As a storage medium for supplying the program codes, a floppy disk, hard disk, optical disk, magnetooptical disk, CD-ROM, CD-R, magnetic tape, nonvolatile memory card, ROM, or the like can be used.

The functions of the above embodiments are implemented not only when the readout program codes are executed by the computer but also when the OS (Operating System) running on the computer performs part or all of actual processing based on the instructions of the program codes. Obviously, the present invention incorporates a case in which the function of the above embodiments are implemented by this processing.

Obviously, the present invention also incorporates a case in which the functions of the above embodiments are also implemented when the program codes read out from the storage medium are written in the memory of a function expansion board inserted into the computer or a function expansion unit connected to the computer, and the CPU 100 or the like of the function expansion board or function expansion unit performs part or all of actual processing based on the instructions of the program codes.

Note that the description of this embodiment is a preferred example of the diagnosis support apparatus according to the present invention, and the present invention is not limited to this.

The arrangement of the present invention can provide a mechanism for obtaining diagnostic information by computer processing with consideration given to the examination history of an object.

The present invention is not limited to the above embodiments and various changes and modifications can be made within the spirit and scope of the present invention. Therefore, to apprise the public of the scope of the present invention, the following claims are made.

This application claims the benefit of Japanese Patent Application No. 2007-271300, filed Oct. 18, 2007 which is hereby incorporated by reference herein in its entirety.

The invention claimed is:

1. A diagnosis support apparatus operably coupled to a medical examination data acquisition apparatus, the diagnosis support apparatus comprising:
    a processor; and
    a memory having stored thereon instructions which, when executed by the processor, cause the processor to:
        obtain examination data of an object from the medical examination data acquisition apparatus;
        process the examination data of the object to extract diagnosis support information;
        store medical examination history of the object in a storage unit;
        calculate an onset probability of a lesion based on the medical examination history of the object;
        determine whether or not the object is taking a first medical examination based on the stored medical examination history of the object, wherein it is determined that the object is taking the first medical examination if the medical examination history of the object does not exist in the storage unit,
        wherein, in a case where it is determined that the object is taking the first medical examination, a lesion of a size in a first range is extracted from the examination data, and
        wherein, in a case where it is determined that the object is not taking the first medical examination, a lesion of a size in a second range smaller than the first range is extracted from the examination data, and wherein the second range is based on the calculated onset probability; and
        control the medical examination data acquisition apparatus to change an acquisition parameter in the medical examination data acquisition apparatus based on the calculated onset probability.

2. The diagnosis support apparatus according to claim 1, wherein the instructions further cause the processor to:

associate and store, in a case database, a feature amount of information of the lesion in a case,
wherein the case database stores an important morbidity A, which is a relative disease severity among different kinds of diseases, a progress degree B, and an associated morbidity C, and
wherein a feature amount from information about the lesion is calculated, and a medical importance of the lesion is obtained from a similarity between the calculated feature amount and a feature amount with a case stored in the case database, wherein a medical importance I is calculated from an equation of I=A*B*C.

3. The diagnosis support apparatus according to claim 1, wherein the second range is changed in accordance with elapsed time.

4. The diagnosis support apparatus according to claim 1, wherein the instructions further cause the processor to output the extracted lesion.

5. A control method performed by a computer for a diagnosis support apparatus operably coupled to a medical examination data acquisition apparatus, the diagnosis support apparatus including a storage unit configured to store medical examination history of an object, the method comprising:
obtaining examination data of an object from the medical examination data acquisition apparatus;
processing the examination data of the object to extract diagnosis support information;
calculating an onset probability of a lesion based on the medical examination history of the object;
determining whether or not the object is taking a first medical examination, based on the medical examination history of the object stored in the storage unit, wherein it is determined that the object is taking the first medical examination if the medical examination history of the object does not exist in the storage unit,
wherein, in a case where it is determined that the object is taking the first medical examination, a lesion of a size in a first range is extracted from the examination data, and
wherein, in a case where it is determined that the object is not taking the first medical examination, a lesion of a size in a second range smaller than the first range is extracted from the examination data, and wherein the second range is based on the calculated onset probability; and
controlling the medical examination data acquisition apparatus to change an acquisition parameter in the medical examination data acquisition apparatus based on the calculated onset probability.

6. A non-transitory computer readable storage medium storing a computer program, which, when executed by a computer for a diagnosis support apparatus operably coupled to a medical examination data acquisition apparatus, the diagnosis support apparatus including a storage unit configured to store medical examination history of an object, causes the computer to perform a method comprising:
obtaining examination data of an object from the medical examination data acquisition apparatus;
processing the examination data of the object to extract diagnosis support information;
calculating an onset probability of a lesion based on the medical examination history of the object;
determining whether or not the object is taking a first medical examination, based on the medical examination history of the object stored in the storage unit, wherein it is determined that the object is taking the first medical examination if the medical examination history of the object does not exist in the storage unit,
wherein, in a case where it is determined that the object is taking the first medical examination, a lesion of a size in a first range is extracted from the examination data, and
wherein, in a case where it is determined that the object is not taking the first medical examination, a lesion of a size in a second range smaller than the first range is extracted from the examination data, and wherein the second range is based on the calculated onset probability; and
controlling the medical examination data acquisition apparatus to change an acquisition parameter in the medical examination data acquisition apparatus based on the calculated onset probability.

7. A diagnosis support apparatus operably coupled to a medical examination data acquisition apparatus, the diagnosis support apparatus comprising:
a processor; and
a memory having stored thereon instructions which, when executed by the processor, cause the processor to:
obtain examination data of an object from the medical examination data acquisition apparatus;
extract, by processing the examination data of the object, a lesion candidate from that data;
determine whether the extracted lesion candidate is malignant or benign;
store medical examination history of the object;
calculate an onset probability of a lesion based on the medical examination history of the object;
change criterion used for determining whether the extracted lesion candidate is malignant or benign, based on the calculated onset probability; and
control the medical examination data apparatus to change an acquisition parameter in the medical examination data acquisition apparatus based on the calculated onset probability.

8. The diagnosis support apparatus according to claim 1, wherein the medical examination data acquisition apparatus is an X-ray CT apparatus, and
wherein the instructions further cause the processor to:
determine whether the onset probability is low or high;
control the X-ray CT apparatus to reduce the dose of an X-ray source of the X-ray CT apparatus or increase the slice intervals obtained by the X-ray CT apparatus when it is determined that the onset probability is low; and
control the X-ray CT apparatus to increase the dose of the X-ray source or decrease the slice intervals obtained by the X-ray CT apparatus when it is determined that the onset probability is high.

* * * * *